United States Patent [19]

Cripe

[11] Patent Number: 5,233,087
[45] Date of Patent: Aug. 3, 1993

[54] PROCESS FOR MAKING ALKYL ETHOXY CARBOXYLATES

[75] Inventor: Thomas A. Cripe, Cincinnati, Ohio

[73] Assignee: The Procter & Gamble Company, Cincinnati, Ohio

[21] Appl. No.: 857,672

[22] Filed: Mar. 25, 1992

Related U.S. Application Data

[63] Continuation of Ser. No. 741,184, Jul. 29, 1991, abandoned, which is a continuation of Ser. No. 354,968, May 22, 1989, abandoned.

[51] Int. Cl.⁵ .............................................. C07C 51/16
[52] U.S. Cl. .................................................. 562/537
[58] Field of Search .......................................... 562/537

[56] References Cited

U.S. PATENT DOCUMENTS

| | | | |
|---|---|---|---|
| 2,623,900 | 12/1962 | Hofer | 562/470 |
| 3,992,443 | 11/1976 | Springmann | 562/470 |
| 4,625,057 | 11/1986 | Springmann et al. | 562/470 |

Primary Examiner—José G. Dees
Assistant Examiner—Samuel Barts
Attorney, Agent, or Firm—Mary P. McMahon; Fernando A. Borrego; Donald E. Hasse

[57] ABSTRACT

An improved process for the production of alkyl ethoxy carboxylate surfactants comprising reacting ethoxylated fatty alcohols with a selective hindered base and anhydrous chloroacetic acid or a salt thereof. The reactants can be reacted simultaneously or, initially, the hindered base can be reacted with the ethoxylated fatty alcohol and, subsequently the resultant product reacted with anhydrous chloroacetic acid or a salt thereof.

18 Claims, No Drawings

PROCESS FOR MAKING ALKYL ETHOXY CARBOXYLATES

This is a continuation of application Ser. No. 741,184, filed on Jul. 29, 1991 now abandoned. which is a continuation of application Ser. No. 354,968 filed on May 22, 1989 now abandoned.

TECHNICAL FIELD

This invention relates to a process for preparing alkyl ethoxy carboxylate surfactants of the type disclosed in U.S. Pat. Nos. 2,183,853; 2,653,972; 3,003,954; 3,038,862; 3,741,911; and 3,941,710; British Patent Nos. 456,517 and 1,169,496; Canadian Patent No. 912,395; French Patent Nos. 2,014,084 and 2.042,793; Netherlands Patent Application Nos. 7,201,735-Q and 7,406,336; and Japanese Patent Application Nos. 96,579/71 and 99,331/71. The invention also relates to cleaning compositions such as shampoos, laundry detergents, and preferably liquid dish washing detergent compositions containing such alkyl ethoxy carboxylate surfactants.

BACKGROUND OF THE INVENTION

Alkyl ethoxy carboxylate surfactants are typically prepared from alkyl polyether nonionic surfactants. Specifically, the alkyl ethoxy carboxylate surfactants are formed by first reacting ethoxylated fatty alcohol with a hydroxide base to deprotonate the alcohol and form the corresponding alkoxide base. The alkoxide is then reacted with a salt of chloroacetic acid to produce the alkyl ethoxy carboxylate. However, the chloroacetic acid salt also has a tendency to react with the hydroxide base in an unwanted side reaction to form a glycolate salt. In order to obtain high conversion of the ethoxylated alcohol to the alkyl ethoxy carboxylate, the reaction must be run at elevated temperature and under reduced pressure so as to drive the equilibrium of the deprotonating reaction toward the alkoxide base and avoid the unwanted side reaction. Alternatively, the reaction may be run using excess hydroxide base and excess chloroacetic acid and subsequently removing the contaminant that is formed by the hydroxide and the chloroacetic acid salt.

It is an object of this invention to provide a process for producing alkyl ethoxy carboxylate surfactants using a selective hindered base in place of a hydroxide base in order to avoid unwanted side reactions and eliminate the need to remove unwanted contaminants.

It is a further object of this invention to provide a process for producing alkyl ethoxy carboxylate surfactants so that a minimal amount of anhydrous chloroacetic acid or a salt thereof is used in converting the ethoxylated alcohol into the alkyl ethoxy carboxylate product.

SUMMARY OF THE INVENTION

The present invention encompasses processes for preparing alkyl ethoxy carboxylate surfactants of the formula

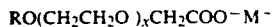

where R is a $C_8$ to $C_{18}$ alkyl group. x is a number averaging from about 1 to 15, and M is an alkali metal or an alkaline earth metal cation; said process comprising, reacting:

(a) an ethoxylated fatty alcohol of the formula $RO(CH_2CH_2O)_xH$, wherein R is a $C_8$ to $C_{18}$ alkyl group and x is a number averaging from about 1 to 15;

(b) a hindered base of the formula $RO^-M^+$, wherein $RO^-$ is a secondary or tertiary alkoxide, R is a non-linear $C_4$ to $C_{12}$ alkyl group with at least one site of branching within 3 carbon atoms of the oxygen atom, and M is an alkali metal or alkaline earth metal cation; and (c) anhydrous chloroacetic acid, at a molar ratio of the hindered base to the anhydrous chloroacetic acid of 2:1, or an alkali metal salt or alkaline earth metal salt of anhydrous chloroacetic acid, at a molar ratio of the hindered base to the alkali metal salt or alkaline earth metal salt of chloroacetic acid of 1:1;

wherein the molar ratio of the ethoxylated fatty alcohol to the anhydrous chloroacetic acid or the alkali metal salt or alkaline earth metal salt thereof is from about 1:0.7 to about 1:1.25, the temperature is from about 20° to 140° C., and the pressure is from about 1 to 760 mm Hg.

DETAILED DESCRIPTION OF THE INVENTION

The alkyl ethoxy carboxylate surfactants of this invention are of the formula

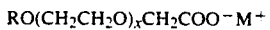

wherein R is a $C_8$ to $C_{18}$ alkyl group, x is a number averaging from about 1 to 15, and M is an alkali metal or an alkaline earth metal cation. The alkyl chain having from about 8 to about 18 carbon atoms can be derived from fatty alcohols, olefins, etc. Normally, and preferably, the alkyl chain will be a mixture of alkyl chains. However, pure alkyl chains can be used. The alkyl chain is desirably a straight saturated alkyl chain, but it may also be a branched and/or unsaturated alkyl chain.

Suitable alcohol precursors of the alkyl ethoxy carboxylate surfactants of this invention are primary aliphatic alcohols containing from about 8 to about 18 carbon atoms. Other suitable primary aliphatic alcohols are the linear primary alcohols obtained from the hydrogenation of vegetable or animal fatty acids such as coconut, palm kernel, and tallow fatty acids or by ethylene build up reactions and subsequent hydrolysis as in the Ziegler type processes. Preferred alcohols are n-octyl, n-nonyl, n-decyl, u-undecyl, n-dodecyl, n-tridecyl, n-tetradecyl, n-pentadecyl, n-hexadecyl, n-heptadecyl, and n-octadecyl. Other suitable alcohol precursors include primary alcohols having a proportion of branching on the beta or 2-carbon atoms wherein the alkyl branch contains from 1 to 4 carbon atoms. In such alcohols at least 30% of the alcohol of each specific chain length is desirably linear and the branching preferably comprises about 50% of methyl groups with smaller amounts of ethyl, propyl and butyl groups. These alcohols are conveniently produced by reaction of linear olefins having from about 11 to 17 carbon atoms with carbon monoxide and hydrogen. Both linear and branched chain alcohols are formed by these processes and the mixtures can either be used as such or can be separated into individual components and then recombined to give the desired blend.

Typical processes for producing "Oxo" halides which are then used to prepare alcohols are disclosed in U.S. Pat. Nos. 2,564,456 and 2,587,858 and the direct hydroformylation of olefins to give alcohols is disclosed in U.S. Pat. Nos. 2,504,682 and 1,581,988. All of these patents are incorporated herein by reference.

The equivalent secondary alcohols can also be used. It will be apparent that by using a single chain length olefin as starting material, a corresponding single chain length alcohol will result, but it is generally more economical to utilize mixtures of olefins having a spread of carbon chain length around the desired mean. This will, of course, provide a mixture of alcohols having the same distribution of chain lengths around the mean.

Primary aliphatic alcohols derived from vegetable oils and fats and from other petroleum feed stocks having alkyl or alkylene groups as part of their structure will also contain a range of chain lengths. Since the range of chain lengths is $C_8-C_{20}$ and beyond, it is therefore normal practice to separate the product from such feed stocks into different chain length ranges which are chosen with reference to their ultimate use.

The ethoxy portion of the surfactant which corresponds to the ethoxy portion of the ethoxylated alcohol reactant desirably contains a chain length averaging from about 1 to 15. A more preferred average ethoxy chain length is from about 2 to 6.

The desired average ethoxy chain length on the ethoxylated fatty alcohol can be obtained by using a catalyzed ethoxylation process, wherein the molar amount of ethylene oxide reacted with each equivalent of fatty alcohol will correspond to the average number of ethoxy groups on the ethoxylated alcohol. The addition of ethylene oxide to alkanols is known to be promoted by a catalyst, most conventionally a catalyst of either strongly acidic or strongly basic character. Suitable basic catalysts are the basic salts of the alkali metals of Group I of the Periodic Table, e.g., sodium, potassium, rubidium, and cesium, and the basic salts of certain of the alkaline earth metals of Group II of the Periodic Table, e.g., calcium, strontium, barium, and in some cases magnesium. Suitable acidic catalysts include, broadly, the Lewis acid of Friedel-Crafts catalysts. Specific examples of these catalysts are the fluorides, chlorides, and bromides of boron, antimony, tungsten, iron, nickel, zinc, tin, aluminum, titanium, and molybdenum. The use of complexes of such halides with, for example, alcohols, ethers, carboxylic acids, and amines have also been reported. Still other examples of known acidic alkoxylation catalysts are sulfuric and phosphoric acids; perchloric acid and the perchlorates of magnesium, calcium, manganese, nickel, and zinc; metals oxalates, sulfates, phosphates, carboxylates, and acetates; alkali metal fluoroborates, zinc titanate; and metal salts of benzene sulfonic acid. The type of catalyst used will determine the distribution of the range of ethoxy groups. Stronger catalysts will result in a very tight or narrow distribution of the ethoxy groups around the mean. Weaker catalysts will result in a wider distribution.

Conventional methods for making alkyl ethoxy carboxylate surfactants use hydroxides to react with the ethoxylated fatty alcohols. The hydroxide deprotonates the alcohol, transforming it into the corresponding alkoxide. A chloroacetic acid salt is added to the reaction mixture, and it reacts with the alkoxide to form the alkyl ethoxy carboxylate. A severe problem with such a method is that the hydroxide, apart from deprotonating the alcohol, also reacts with the chloroacetic acid salt to form a glycolate salt, a very undesirable by-product.

Therefore, it is required to run this reaction at elevated temperatures and reduced pressures to drive the deprotonating reaction toward the alkoxide in order to leave a minimal amount of hydroxide in the reaction mixture to react with the chloroacetic acid salt. An alternative or complementary method involves using excess hydroxide and excess chloroacetic acid salt, then removing the contaminant, glycolate salt, after completion of the reaction.

Consequently, an alternative to the use of the hydroxide to deprotonate the fatty alcohol was investigated and designed herein. It was discovered that the base's pKa (measurement of the reactiveness of a molecule) must be great enough to allow it to deprotonate the fatty alcohol, leaving it in a form to react with the chloroacetate. Concurrently, the base must have sufficient adjuncts attached to the reactive oxygen atom to inhibit any reaction with the chloroacetate ion.

The hindered base of this invention is represented by the formula $RO^-M^+$, constituting generally an alkyl group, a reactive oxygen center, and a cation. The structure of this hindered base is secondary or tertiary. The base contains a non-linear alkyl group with at least one site of branching within 3 carbon atoms of the reactive center, the oxygen atom, and an alkali metal or alkaline earth metal adjunct. The preferred hindered base is a tertiary material containing less than 6 carbon atoms. Most preferably it is tert-butoxide, which is sufficiently reactive to strip a hydrogen atom off the fatty alcohol, yet contains a tertiary alkyl attached to the reactive oxygen atom that inhibits it from reacting with the chloroacetate ion. Instead, the t-butoxide combines with the hydrogen from the alcohol to form t-butanol which is easily removed from the resultant mixture.

Anhydrous chloroacetic acid may be used to combine with the alkoxide to form the alkyl ethoxy carboxylate but aqueous chloroacetic acid may not be utilized. The reason for this is that aqueous chloroacetic acid contains water which, under the reaction conditions, generates hydroxide ions. This necessarily revives the complications associated with the method described above, i.e., the formation of unwanted side product, glycolate salt, from hydroxide reacting with chloroacetate. Thus chloroacetic acid must be used in the anhydrous state, but this requires the use of 2 equivalents of the hindered base for every equivalent of anhydrous chloroacetic acid. This 2 to 1 ratio is necessary because, in addition to deprotonating the fatty alcohol, the base must also deprotonate the chloroacetic acid to form the chloroacetate anion that is needed to react with the alkoxide to form the alkyl ethoxy carboxylate.

The preferred form of chloroacetic acid is its alkali metal salt or alkaline earth metal salt. Most preferred of these are sodium chloroacetate, potassium chloroacetate, or a combination thereof. These acetates require only one equivalent of the hindered base for every equivalent of the chloroacetate.

The ethoxylated fatty alcohol must be put in the reaction mixture at a molar ratio of the alcohol to the anhydrous chloroacetic acid or alkali metal salt or alkaline earth metal salt thereof of from approximately 1:0.7 to 1:1.25, preferably from about 1:1 to about 1:1.15.

Temperature and pressure controls in the process of this invention increase the rate of reaction. For example, the reaction of the present invention can be run at between 20 and 140° C. and under a pressure of 1 to 760 mm Hg, preferably at 60 to 120° C. and under a pressure of 15 to 350 mm Hg, if an increased rate of reaction is desired. In contrast, conventional methods of making alkyl ethoxy carboxylate surfactants must be performed at elevated temperatures and reduced pressures in order to avoid the undesirable glycolate side reaction.

Furthermore, the process of this invention can attain very specific levels of conversion of the ethoxylated fatty alcohol to the alkyl ethoxy carboxylate of from about 70% to 100% without rigorous controls on the reaction temperature and/or pressure and without huge excesses of the reactants. The conventional methods for making alkyl ethoxy carboxylate surfactants generally require excesses of the hydroxide and chloroacetic acid in addition to the above requirement of elevated temperatures and reduced pressures.

This advantage over conventional methods for making alkyl ethoxy carboxylate surfactants becomes very prominent when the desired conversion of the alcohol to the alkyl ethoxy carboxylate is above 90%. Under that parameter, the conventional methods require excesses of the hydroxide and chloroacetic acid (sometimes above 100%) and/or rigorous temperature and pressure controls. Using tert-butoxide, the process of this invention requires only minimal temperature and pressure controls (only for purposes of speeding up the reaction rate) and, at most, excesses of the tert-butoxide and chloroacetate of from about 10% to 25%.

The resultant product may be subjected to a working-up procedure depending on the end use desired. For certain uses, for example for tenside flooding, it is possible to use the resultant crude product directly. In such case it is unnecessary to separate the sodium or potassium chloride formed as a by-product. However, if such a separation is desired, it is possible to do so by adding the reaction mixture to a sufficiently strong aqueous solution of hydrochloric or sulfuric acid so that the final pH is between 2 and 4. The mixture will phase separate, at room temperature, into an organic upper phase containing the free acid, which can be easily separated from the lower, aqueous phase containing any unreacted chloroacetate and inorganic salts in dissolved form (U.S. Pat. No. 3,992,443, Column 4, lines 6-11). A greater degree of separation, in a markedly shorter period of time, will occur if the mixture is heated. Thereafter, the alkyl ethoxy carboxylic acid can be neutralized by adding the upper layer phase mixture to a sufficiently strong aqueous solution of sodium hydroxide, potassium hydroxide, or ammonium hydroxide so that the final pH is about 7 to 10.

The alkyl ethoxy carboxylate surfactants produced by the present invention can be used in any compositions known in the art to contain such surfactants. They are preferably used in cleaning compositions such as shampoos, laundry detergents, and liquid dish washing detergent compositions. Such compositions are disclosed in, for example, U.S. Pat. Nos. 4,486,338 (Ootani et al) and 3,941,710 (Gilbert et al); and Japanese Patent Applications 48-60706 and 48-64102 (both Kao patents), all incorporated herein by reference.

Preferred light-duty liquid dish washing detergent compositions herein comprise from about 5% to 50% of a surfactant mixture comprising:
  (a) from about 80% to 100% of alkyl ethoxy carboxylates of the formula:

$RO(CH_2CH_2O)_xCH_2COO^-M^-$ wherein R is a $C_{12}$ to $C_{16}$ alkyl group, x ranges from 0 to about 10 and the ethoxylate distribution is such that, on a weight basis, the amount of material where x is 0 is less than about 20% and the amount of material where x is greater than 7 is less than about 25%, the average x is from about 2 to 4 when the average R is $C_{13}$ or less, and the average x is from about 3 to 6 when the average R is greater than $C_{13}$, and M is a cation;
  (b) from 0% to about 10% of alcohol ethoxylates of the formula:

$RO(CH_2CH_2O)_xH$ wherein R is a $C_{12}$ to $C_{16}$ alkyl group and x ranges from 0 to about 10 and the average x is less than about 6; and
  (c) from 0% to10 about 10% of soaps of the formula:

$RCOO^-M^+$ wherein R is a $C_{11}$ to $C_{15}$ alkyl group and M is a cation;
said composition having a pH from about 7 to 11.

The above light-duty liquid dish washing detergent compositions contain a surfactant mixture comprising a major amount of an alkyl ethoxy carboxylate surfactant and little or no alcohol ethoxylate and soap by-product contaminants. These and other complementary optional ingredients typically found in liquid dish washing compositions are set forth below.

The above composition contains from about 5% to 50% by weight, preferably from about 10% to 40%, most preferably from about 12% to 30%, of a surfactant mixture restricted in the levels of contaminants.

The surfactant mixture contains from about 80% to 100%, preferably from about 85% to 95%, most preferably from about 90% to 95%, of alkyl ethoxy carboxylates of the generic formula $RO(CH_2CH_2O)_xCH_2COO^-M^+$ wherein R is a $C_{12}$ to $C_{16}$ alkyl group, x ranges from 0 to about 10, and the ethoxylate distribution is such that, on a weight basis, the amount of material where x is 0 is less than about 20%, preferably less than about 15%, most preferably less than about 10%, and the amount of material where x is greater than 7 is less than about 25%, preferably less than about 15%, most preferably less than about 10%, the average x is from about 2 to 4 when the average R is $C_{13}$ or less, and the average x is from about 3 to 6 when the average R is greater than $C_{13}$, and M is a cation, preferably chosen from alkali metal, alkaline earth metal, ammonium, mono-, di-, and tri-ethanolammonium, most preferably from sodium, potassium, ammonium, and mixtures thereof with magnesium ions. The preferred alkyl ethoxy carboxylates are those where R is a $C_{12}$ to $C_{14}$ alkyl group.

The surfactant mixture also contains from 0% to about 10%, preferably less than about 8%, most preferably less than about 5%, of alcohol ethoxylates of the formula $RO(CH_2CH_2O)_xH$ wherein R is a $C_{12}$ to $C_{16}$ alkyl group and x ranges from 0 to about 10 and the average x is less than about 6. The surfactant mixture also contains 0% to about 10%, preferably less than about 8%, most preferably less than about 5%, of soaps of the formula $RCOO^-M^+$ wherein R is a $C_{11}$ to $C_{15}$ alkyl group and M is a cation as described above.

The uncarboxylated alcohol ethoxylates noted above are a detriment to the alkyl ethoxy carboxylate surfactant mixture. Therefore, it is critical that the alkyl ethoxy carboxylate-containing surfactant mixture used in this invention contain less than about 10% by weight of the alcohol ethoxylates they are derived from.

The above compositions have a pH from about 7 to 11, determined as the pH of the undiluted composition with a pH meter. The preferred detergent composition has a pH from about 8 to 10.5 and most preferably from about 8.5 to 10. Traditionally, liquid dish washing compositions have a pH of about 7. It has been found for detergent compositions herein that a more alkaline pH of about 9 greatly improves the grease cleaning as compared to a product with a pH of 7. This cleaning benefit appears to be unique to compositions containing the present alkyl ethoxy carboxylates. Surprisingly, these compositions are still very mild to hands at an alkaline pH.

If a composition with a pH greater than 7 is to be most effective in improving performance, it should contain a buffering agent capable of maintaining the alkaline pH in the composition and in dilute solutions of the composition. This buffering agent may be an active detergent in its own right, or it may be a low molecular weight, organic or inorganic material that is used in this composition solely for maintaining an alkaline pH. Preferred buffering agents for compositions of this invention are nitrogen-containing materials. Some examples are glycine or other amino acids or lower alcohol amines like mono-, di-, and tri-ethanolamine. These buffering agents are typically present at a level of from about 0.1% to 10% by weight, preferably from about 1% to 7%, most preferably from about 1.5% to 5%.

The cations for the alkyl ethoxy carboxylates herein can be alkali metals, alkaline earth metals, ammonium, and lower alkanol ammonium ions. It has been found that for the present alkyl ethoxy carboxylates the presence of divalent cations greatly improves the cleaning of greasy soils. This is especially true when the compositions are used in softened water that contains few divalent ions. Dish washing liquid compositions that contain alkyl ethoxy carboxylates that do not conform to the above narrow definition will be less benefited by the addition of divalent ions and, in many cases, will actually exhibit reduced cleaning performance upon the addition of divalent cations. It is believed that divalent ions increase the packing of the present alkyl ethoxy carboxylates at the oil/water interface, thereby reducing interfacial tension and improving grease cleaning.

Preferably, the divalent ions are added as a chloride or sulfate salt to compositions containing an alkali metal or ammonium salt of the alkyl ethoxy carboxylate, most preferably the sodium salt, after the composition has been neutralized with a strong base. The level of divalent ion in the composition is from 0% to about 1.5%, preferably from about 0.2% to 1%, most preferably from about 0.3% to 0.8%, by weight. Particularly preferred divalent ions are magnesium ions.

When both divalent ions and alkaline pH are combined with the surfactant mixture herein, grease cleaning is achieved that is superior to that obtained by either alkaline pH or divalent ions alone. Preferably, the divalent ion is magnesium, present in the composition at a level of from about 0.1% to 1%, most preferably from about 0.3% to 0.8%, by weight, while the pH is preferably from about 8 to 9.5 and most preferably from about 8.5 to 9.5. Compositions that contain higher levels of magnesium and have a pH much above about 9.5 are not preferred due to a tendency to form precipitates.

Co-Surfactants

The compositions herein preferably contain certain co-surfactants to aid in the foaming, detergency, and/or mildness.

Included in this category are several anionic surfactants commonly used in liquid dish washing detergents. The cations associated with these anionic surfactants can be the same as the cations described previously for the alkyl ethoxy carboxylates. Examples of anionic co-surfactants that are useful herein are the following classes:

(1) Alkyl benzene sulfonates in which the alkyl group contains from 9 to 15 carbon atoms, preferably 11 to 14 carbon atoms in straight chain or branched chain configuration. An especially preferred linear alkyl benzene sulfonate contains about 12 carbon atoms. U.S. Pat. Nos. 2,220,099 and 2,477,383 describe these surfactants in detail.

(2) Alkyl sulfates obtained by sulfating an alcohol having 8 to 22 carbon atoms, preferably 12 to 16 carbon atoms. The alkyl sulfates have the formula $RO-SO_3^-M^+$ where R is the $C_{8-22}$ alkyl group and M is a mono- and/or divalant cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having to 22 carbon atoms, preferably 12 to 16 carbon atoms. U.S. Pat. No. 3,332,880 contains a description of suitable olefin sulfonates.

(5) Alkyl ether sulfates derived from ethoxylating an alcohol having 8 to 22 carbon atoms, preferably 12 to 16 carbon atoms, less than 30, preferably less than 12, moles of ethylene oxide. The alkyl ether sulfates having the formula:

$$RO(C_2H_4O)_xSO_3^-M^+$$

where R is the $C_{8-22}$ alkyl group, x is 1-30, and M is a mono- or divalent cation.

(6) Alkyl glyceryl ether sulfonates having 8 to 22 carbon atoms, preferably 12 to 16 carbon atoms, in the alkyl moiety.

(7) Dialkyl sulfosuccinates of the formula:

$$\begin{array}{c} CH_2\text{---}CH\text{---}SO_3^-M^+ \\ | \quad\quad | \\ COOR_1 \quad COOR_2 \end{array}$$

where each of $R_1$ and $R_2$, which may be the same or different, represents a straight chain or branched chain alkyl group having from about 4 to 10 carbon atoms and more preferably from about 6 to 8 carbon atoms, and $M^+$ represents a mono-or divalent cation. A more complete description of suitable dialkyl sulfosuccinates can be found in GB 2,105,325 and GB 2,104,913.

(8) Fatty acid ester sulfonates of the formula:

$$R_1\text{---}CH(SO_3^-M^+)CO_2R_2$$

wherein $R_1$ is straight or branched alkyl from about $C_8$ to $C_{18}$, preferably $C_{12}$ to $C_{16}$, and $R_2$ is straight or branched alkyl from about $C_1$ to $C_6$, preferably primarily $C_1$, and $M^+$ represents a mono or divalent cation.

(9) Mixtures thereof.

The above described anionic surfactants are all available commercially. It should be noted that although both dialkyl sulfosuccinates and fatty acid ester sulfonates will function well at neutral to slightly alkaline pH, they will not be chemically stable in a composition with pH much greater than about 8.5.

Other useful co-surfactants for use in the compositions are the nonionic fatty alkylpolyglucosides. These surfactants contain straight chain or branched chain $C_8$ to $C_{15}$, preferably from about $C_{12}$ to $C_{14}$, alkyl groups and have an average of from about 1 to 5 glucose units, with an average of 1 to 2 glucose units being most preferred. U.S. Pat. Nos. 4,393,203 and 4,732,704, incorporated by reference, describe these surfactants.

The co-surfactants for the compositions herein can also contain mixtures of anionic surfactants with alkyl polyglucosides. The co-surfactants are present in the composition at a level of from 0% to about 35% by weight, preferably from about 5% to 25%, and most preferably from about 7% to 20%.

Suds Booster

Another component which may be included in the compositions is a suds stabilizing surfactant (suds booster) at a level of less than about 15%, preferably from about 0.5% to 12%, more preferably from about 1% to 10%. Optional suds stabilizing surfactants operable in the instant composition are of five basic types—betaines, ethylene oxide condensates, fatty acid amides, amine oxide semi-polar nonionics, and cationic surfactants.

The compositions can contain betaine detergent surfactants having the general formula:

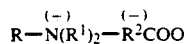

wherein R is a hydrophobic group selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring being treated as equivalent to about 2 carbon atoms, and similar structures interrupted by amido or ether linkages; each $R^1$ is an alkyl group containing from 1 to about 3 carbon atoms; and $R^2$ is an alkylene group containing from 1 to about 6 carbon atoms.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate.

Other suitable amidoalkylbetaines are disclosed in U.S. Pat. Nos. 3,950,417; 4,137,191; and 4,375,421; and British Patent GB No. 2,103,236, all of which are incorporated herein by reference.

It will be recognized that the alkyl (and acyl) groups for the above betaine surfactants can be derived from either natural or synthetic sources, e,g., they can be derived from naturally occurring fatty acids; olefins such as those prepared by Ziegler, or Oxo processes; or from olefins separated from petroleum either with or without "cracking".

The ethylene oxide condensates are broadly defined as compounds produced by the condensation of ethylene oxide groups (hydrophilic in nature) with an organic hydrophobic compound, which can be aliphatic or alkyl aromatic in nature. The length of the hydrophilic or polyoxyalkylene radical which is condensed with any particular hydrophobic group can be readily adjusted to yield a water-soluble compound having the desired balance between hydrophilic and hydrophobic elements.

Examples of such ethylene oxide condensates suitable as suds stabilizers are the condensation products of aliphatic alcohols with ethylene oxide. The alkyl chain of the aliphatic alcohol can either be straight or branched and generally contains from about 8 to about 18, preferably from about 8 to about 14, carbon atoms for best performance as suds stabilizers, the ethylene oxide being present in amounts of from about 8 moles to about 30, preferably from about 8 to about 14 moles of ethylene oxide per mole of alcohol.

Examples of the amide surfactants useful herein include the ammonia, monoethanol, and diethanol amides of fatty acids having an acyl moiety containing from about 8 to about 18 carbon atoms and represented by the general formula:

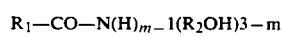

wherein R is a saturated or unsaturated, aliphatic hydrocarbon radical having from about 7 to 21, preferably from about 11 to 17 carbon atoms; $R_2$ represents a methylene or ethylene group; and m is 1, 2, or 3. preferably 1. Specific examples of said amides are mono-ethanol amine coconut fatty acid amide and diethanol amine dodecyl fatty acid amide. These acyl moieties may be derived from naturally occurring glycerides, e.g., coconut oil, palm oil, soybean oil, and tallow, but can be derived synthetically, e.g., by the oxidation of petroleum or by hydrogenation of carbon monoxide by the Fischer-Tropsch process. The monoethanol amides and diethanolamides of $C_{12-14}$ fatty acids are preferred.

Amine oxide semi-polar nonionic surfactants comprise compounds and mixtures of compounds having the formula

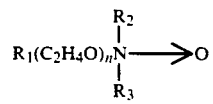

wherein $R_1$ is an alkyl, 2-hydroxyalkyl, 3-hydroxyalkyl, or 3-alkoxy-2-hydroxypropyl radical in which the alkyl and alkoxy, respectively, contain from about 8 to about 18 carbon atoms, $R_2$ and $R_3$ are each methyl, ethyl, propyl, isopropyl, 2-hydroxyethyl, 2-hydroxypropyl, or 3-hydroxypropyl, and n is from 0 to about 10. Particularly preferred are amine oxides of the formula:

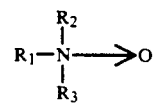

wherein $R_1$ is a $C_{12-16}$ alkyl and $R_2$ and $R_3$ are methyl or ethyl. The above ethylene oxide condensates, amides, and amine oxides are more fully described in U.S. Pat. No. 4,316,824 (Pancheri), incorporated herein by reference.

The compositions can also contain certain cationic quarternary ammonium surfactants of the formula:

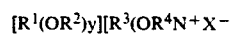

or amine surfactants of the formula:

[R$^1$(OR$^2$)y][R$^3$(OR$^2$)y]R$^4$N wherein R$^1$ is an alkyl or alkyl benzyl group having from about 6 to about 16 carbon atoms in the alkyl chain; each R$^2$ is selected from the group consisting of —CH$_2$CH$_2$—, —CH$_2$CH(CH$_3$)—, —CH$_2$CH(CH$_2$OH)—, —CH$_2$CH$_2$CH$_2$—, and mixtures thereof; each R$^3$ is selected from the group consisting of C$_1$–C$_4$ alkyl, C$_1$–C$_4$ hydroxyalkyl, benzyl, and hydrogen when y is not 0; R$^4$ is the same as R$^3$ or is an alkyl chain wherein the total number of carbon atoms of R$^1$ plus R$^4$ is from about 8 to about 16; each y is from 0 to about 10, and the sum of the y values is from 0 to about 15; and X is any compatible anion.

Preferred of the above are the alkyl quaternary ammonium surfactants, especially the mono-long chain alkyl surfactants described in the above formula when R$^4$ is selected from the same groups as R$^3$. The most preferred quaternary ammonium surfactants are the chloride, bromide, and methylsulfate C$_{8-16}$ alkyl trimethylammonium salts, C$_{8-16}$ alkyl di(hydroxyethyl)-methylammonium salts, the C$_{8-16}$ alkyl hydroxyethyl-dimethylammonium salts, C$_{8-16}$ alkyloxypropyl trimethylammonium salts, and the C$_{8-16}$ alkyloxypropyl dihydroxyethylmethylammonium salts. Of the above, the C$_{10-14}$ alkyl trimethylammonium salts are preferred, e.g., decyl trimethylammonium methylsulfate, lauryl trimethylammonium chloride, myristyl trimethylammonium bromide and coconut trimethylammonium chloride, and methylsulfate.

The suds boosters used in the composition can contain any one or mixture of the suds boosters listed above.

Additional Optional Ingredients

In addition to the ingredients described hereinbefore, the compositions can contain other conventional ingredients suitable for use in liquid dish washing compositions.

Optional ingredients include drainage promoting ethoxylated nonionic surfactants of the type disclosed in U.S. Pat. No. 4,316,824, Pancheri (Feb. 23, 1982), incorporated herein by reference.

Others include detergency builders, either of the organic or inorganic type. Examples of water-soluble inorganic builders which can be used, alone or in admixture with themselves or with organic alkaline sequestrant builder salts, are alkali metal carbonates, phosphates, polyphosphates, and silicates. Specific examples of such salts are sodium tripolyphosphate, sodium carbonate, potassium carbonate, sodium pyrophosphate, potassium pyrophosphate, potassium tripolyphosphate, and sodium hexametaphosphate. Examples of organic builder salts which can be used alone, or in admixture with each other or with the preceding inorganic alkaline builder salts, are alkali metal polycarboxylates, e.g., water-soluble citrates such as sodium and potassium citrate, sodium and potassium tartrate, sodium and potassium ethylenediaminetetraacetate, sodium and potassium N-(2-hydroxyethyl)-ethylene diamine triacetates, sodium and potassium nitrilo triacetates (NTA), sodium and potassium N-(2-hydroxyethyl)-nitrilo diacetates, sodium and potassium oxydisuccinates, and sodium and potassium tartrate mono- and di-succinates, such as described in U.S. Pat. No. 4,663,071 (Bush et al., issued May 5, 1987), incorporated herein by reference. Other organic detergency builders such as water-soluble phosphonates can find use in the compositions of the invention. In general, however, detergency builders have limited value in dish washing detergent compositions, and use at levels above about 10% can restrict formulation flexibility in the liquid compositions herein because of solubility and phase stability considerations.

Alcohols, such as ethyl alcohol and propylene glycol, and hydrotropes, such as sodium and potassium toluene sulfonate, sodium and potassium xylene sulfonate, trisodium sulfosuccinate, and related compounds (as disclosed in U.S. Pat. No. 3,915,903, incorporated herein by reference), and urea, can be utilized in the interests of achieving a desired product phase stability and viscosity. Alcohols such as ethyl alcohol and propylene glycol at a level of from 0% to about 15%, potassium or sodium toluene, xylene, or cumene sulfonate at a level of from 0% to about 10% and urea at a level of from 0% to about 10% are particularly useful in the compositions.

Other desirable ingredients include diluents and solvents. Diluents can be inorganic salts, such as sodium sulfate, ammonium chloride, sodium chloride, sodium bicarbonate, etc., and the solvents include water, lower molecular weight alcohols, such as ethyl alcohol, isopropyl alcohol, etc. Compositions herein will typically contain up to about 80%, preferably from about 30% to about 70%, most preferably from about 40% to about 65%, of water.

As used herein, all percentages, parts, and ratios are by weight unless otherwise state.

The following Examples illustrate the processes of the invention and facilitate its understanding.

EXAMPLE I

An alkyl ethoxy carboxylate surfactant of the formula RO(CH$_2$CH$_2$O )$_x$CH$_2$COO$^-$M$^+$ wherein R is a C$_{12-13}$ alkyl, the average x is 3, and M is sodium, is synthesized by performing the following procedure. 1.1 moles of potassium tert-butoxide is reacted with 1 mole of C$_{12-13}$ alkyl ethoxylate containing on average three ethoxy groups (Neodol 23-3) at 45° C. for 1 hour, while stirring, under reduced pressure of about 17 mm Hg. Tertiary butanol that is pulled off is collected in a dry ice-/acetone trap. At the end of 1 hour, 1.1 moles of sodium chloroacetate is added to the Neodol 23-3/potassium t-butoxide mixture. The reaction temperature is increased to 90° C. and the pressure again reduced to about 17 mm Hg. The reaction mixture is stirred under these conditions overnight. The alkyl ethoxy carboxylate is isolated by adding the reaction mixture to an aqueous solution of HCl so that the pH is about 3, heating the mixture to 90° C., and collecting the upper layer of the two-phase system. Upon analysis, the % conversion of alkyl ethoxylate to alkyl ethoxy carboxylate is greater than 90%. This upper layer phase mixture is added to an aqueous solution of sodium hydroxide so that the pH is about 8.

EXAMPLE II

An alkyl ethoxy carboxylate surfactant of the formula RO(CH$_2$CH$_2$O)$_x$CH$_2$COO$^-$M$^+$ wherein R is a C$_{14-15}$ alkyl, the average x is 5.4, and M is sodium, is made by following the process in Example I but replacing the C$_{12-13}$ alkyl ethoxylate (Neodol 23-3) with a C$_{14-15}$ alkyl ethoxylate containing an average 5.4 ethoxy groups (Neodol 23-5.4). Upon analysis, the % conversion of ethoxylate to alkyl ethoxy carboxylate is greater than 90%.

EXAMPLE III

An alkyl ethoxy carboxylate surfactant similar to the one made in Example I is made when the process in Example I is repeated with the alkyl ethoxylate, potassium tert-butoxide, and sodium chloroacetate added simultaneously at the start of the reaction. The temperature is slowly increased to about 90° C. and the reaction pressure dropped gradually to about 17 mm Hg. The remaining procedure and results are similar to that given in Example I.

Other processes of the present invention are obtained when the potassium tert-butoxide in the above examples is replaced with tertiary pentryl or hexyl alkoxide.

Other processes of the present invention are obtained when the sodium chloroacetate in the above examples is replaced with anhydrous chloroacetic acid, at a molar ratio of the hindered base to the chloroacetic acid of 2:1.

EXAMPLE IV

The following three liquid dish washing detergent compositions contain alkyl ethoxy carboxylate surfactants made by a process of this invention.

Formulation A is made by adding ethanol, sodium chloride, and sodium xylene sulfonate to the alkyl ethoxy carboxylate-containing surfactant mixture. The remaining surfactants are then added and mixed in. Glycine is then added and the pH is adjusted to about 10 with sodium hydroxide. Finally, the magnesium chloride is added, which reduces the pH to about 9.5. Final viscosity and pH adjustments can be made at this time, followed by the addition of perfume and dye. The balance is water.

Formulation B is made by adding ethanol, sodium chloride, and sodium xylene sulfonate to the sodium alkyl ethoxy carboxylate. The remaining formula components are added in the order given in the table.

Formulation C is made by adding ethanol, sodium chloride, and sodium xylene sulfonate to the sodium salt of alkyl ethoxy carboxylate. The alkyl glucoside is mixed in and the temperature of the mixture raised to about 40° C. The coconut monoethanolamine amide is warmed to about 65° C. and mixed in. Minor pH and viscosity adjustments are made at this time, followed by the addition of dye and perfume and water to bring the formulation to 100%.

| Components | % By Weight | | |
|---|---|---|---|
| | Formulation A | Formulation B | Formulation C |
| Sodium $C_{12-13}$ alkyl ethoxy (2.8 ave.) carboxylate* | 15 | 15 | 15 |
| $C_{12-13}$ alkyl ethoxy (2.8 ave.) alcohol* | 0.97 | 0.97 | 0.97 |
| Sodium $C_{12-13}$ alkyl ethoxy (0.8 ave.) sulfate | 15 | — | — |
| Sodium $C_{12-14}$ fatty acid α-sulfonate methyl ester | — | 15 | — |
| $C_{12-13}$ alkyl polyglucoside (1.4 ave.) | — | — | 15 |
| $C_{12-14}$ alkyl dimethyl betaine | 4.0 | — | — |
| $C_{12-14-16}$ alkyl dimethyl amine oxide | — | 4.0 | — |
| $C_{12-14}$ fatty acid monoethanolamine amide | — | — | 4.0 |
| Magnesium ion (added as $MgCl_2 \cdot 6H_2O$) | 0.76 | 0.76 | — |
| Glycine | 4.0 | — | — |
| Sodium xylene sulfonate | 2.0 | 2.2 | 2.0 |
| Ethanol | 7.5 | 7.0 | 7.0 |
| Sodium chloride | 1.5 | <1 | 2.25 |
| Product pH | 9.5 | 7.55 | 7.05 |
| Perfume and dye | 0.15 | 0.15 | 0.15 |
| Water | Balance | Balance | Balance |

*The surfactant mixture containing sodium alkyl ethoxy carboxylate and alkyl ethoxy alcohol is prepared according to the process outlined below:

1. A $C_{12-13}$ alkyl ethoxy (3.0 ave.) alcohol is reacted with potassium t-butoxide and sodium chloroacetate in the ratio of 1:1.1:1.1 by first mixing the alkyl ethoxylate with the potassium t-butoxide at about 60° C. and about 20 mm Hg pressure for about 1 hour. Hereinafter, t-butanol is continuously removed from the reaction mixture by distillation. Thereafter, the vacuum is broken and sodium chloroacetate is added with mixing. The pressure is reestablished at about 18-20 mm Hg, and the reaction is allowed to continue for about 3 hours. Afterwards, the reaction pressure is brought to atmospheric level with nitrogen, and the steam heating coils are turned off. The reaction is left in this state overnight. The next day the reaction mixture temperature is increased and the pressure reduced to remove more t-butanol from the system. The reaction mixture is then added to an aqueous solution of hydrochloric acid containing 105% of the theoretical amount needed to neutralize the potassium t-butoxide initially added. The acid aqueous reaction product is heated to force phase separation of the organic and aqueous materials. The organic phase is collected.

2. Step 1 above is repeated using a $C_{12-13}$ alkyl ethoxy (2.7 ave.) alcohol and a ratio of this ethoxy alcohol to potassium t-butoxide and sodium chloroacetate of 1:1.3:1.3. The potassium t-butoxide is added to the alkyl ethoxylate, which is at a temperature of about 32.2° C., and the reaction mixture is then increased to about 76.7° C. The vacuum pump is then turned on to achieve reduced pressure. The reaction temperature is increased to about 104.4° C., and the t-butanol is pulled off and collected over about a 30 minute period. The sodium chloroacetate is then added to the reation mixture, which has been cooled slightly to about 66° C. The reaction is mixed for about 1.5 hours, cooled, and added to an aqueous solution of sufficient hydrochloric acid to achieve a pH of 3.4. Water is added to increase the volume of the reaction mixture by about 50%, and the mixture is then heated to about 49° C. The top organic layer is collected, and the washing process is repeated.

3. The surfactant mixtures produced in Steps 1 and 2 above are mixed at a ratio of 40.4 to 59.6. A portion of this larger combined surfactant mixture is neutralized with 50% sodium hydroxide to a pH of about 8 and diluted by about 50% with a 25/75 by volume mixture of water and ethanol. The resulting solution is continuously extracted at room temperature with hexanes for about four days. The lower aqueous phase is collected, and some ethanol and water is removed by heating to yield a paste containing the alkyl ethoxy carboxylate containing surfactant mixture described below.

In the above, the surfactant portion of the above mixture contains about 93.9% alkyl ethoxy carboxylates of the formula $RO(CH_2CH_2O)_xCH_2COO^-Na^+$ where R is a $C_{12-13}$ alkyl averaging 12.5; x ranges from 0 to about 10, and the ethoxylate distribution is such that the amount of material where x is 0 is about 2.8% and the amount of material where x is greater than 7 is less than about 2% by weight of the alkyl ethoxy carboxylates. The average x in the distribution is 2.8. The surfactant mixture also contains about 6.1% of alcohol ethoxylates of the formula $RO(CH_2CH_2O)_xH$ with R being a $C_{12-13}$ alkyl averaging 12.5 and the average x=2.8. The surfactant mixture contains 0% soap materials.

The above formulations provide an excellent combination of grease cleaning and mildness benefits. Using the alkyl ethoxy carboxylate-containing surfactant mixture as a building block, a range of good grease cleaning is achieved with the rank order being Formulation A>Formulation B>Formulation C. These same formulations provide a range of mildness benefits with the rank order being Formulation C > Formulation B > Formulation A.

EXAMPLE V

The following formulation containing the surfactant mixture used in Example I comprising the same alkyl ethoxy carboxylates provides exceptional grease cleaning and hand mildness, with sudsing somewhat less than Formulations A, B, and C.

| Components | Formulation D (Wt. %) |
|---|---|
| Sodium $C_{12-13}$ alkyl ethoxy (2.8 ave.) carboxylate | 28 |
| $C_{12-13}$ alkyl ethoxy (2.8 ave.) alcohol | 1.8 |
| Magnesium ion (added as $MgCl_2 \cdot 6H_2O$) | 0.6 |
| Glycine | 4.0 |
| Sodium xylene sulfonate | 2.0 |
| Ethanol | 7.5 |
| Sodium chloride | 1.5 |
| Product pH | 9.0 |
| Perfume and dye | 0.15 |
| Water | Balance |

What is claimed is:

1. A process for preparing an alkyl ethoxy carboxylate surfactant of the formula $$RO(CH_2CH_2O)_xCH_2COO^-M^-$$

wherein R is a $C_8$ to $C_{18}$ alkyl group, x is a number averaging about 1 to 15, and M is an alkali metal or an alkaline earth metal cation; said process comprising, reacting:
   (a) an ethoxylated fatty alcohol of the formula $RO(CH_2CH_2O)_xH$, wherein R is a $C_8$ to $C_{18}$ alkyl group and x is a number averaging from about 1 to 15;
   (b) a hindered base of the formula $RO^-M^+$, wherein $RO^-$ is a secondary or tertiary alkoxide, R is a non-linear $C_4$ to $C_{12}$ alkyl group with at least one site of branching within 3 carbon atoms of the oxygen atom, and M is an alkali metal or alkaline earth metal cation; and
   (c) anhydrous chloroacetic acid, at a molar ratio of the hindered base to the anhydrous chloroacetic acid of 2:1, or an alkali metal salt or alkaline earth metal salt of anhydrous chloroacetic acid, at a molar ratio of the hindered base to the alkali metal salt or alkaline earth metal salt of chloroacetic acid of 1:1;
wherein the molar ratio of the ethoxylated fatty alcohol to the anhydrous chloroacetic acid or the alkali metal salt or alkaline earth metal salt thereof is from about 1:0.7 to about 1:1.25, the temperature is from about 76.7° to 109.4° C., and the pressure is from about 1 to 760 mm Hg.

2. The process of claim 1 wherein in the ethoxylated fatty alcohol R is a $C_{12}$ to $C_{16}$ alkyl group and x averages from about 2 to about 6.

3. The process of claim 1 wherein the hindered base is a tertiary alkoxide salt.

4. The process of claim 3 wherein the hindered base is tert-butoxide salt.

5. The process of claim 1 wherein (c) is potassium chloroacetate, sodium chloroacetate, or a combination thereof.

6. The process in claim 1 wherein in the ethoxylated fatty alcohol R is a $C_{12}$ to $C_{16}$ alkyl group and x averages from about 2 to about 6, and the hindered base is a tert-butoxide salt.

7. The process in claim 1 wherein in the ethoxylated fatty alcohol R is a $C_{12}$ to $C_{15}$ alkyl group and x averages from about 2 to about 6, and (c) is potassium chloroacetate, sodium chloroacetate, or a combination thereof.

8. The process in claim 1 wherein the hindered base is a tert-butoxide salt and (c) is potassium chloroacetate, sodium chloroacetate, or a combination thereof.

9. The process in claim 8 wherein in the ethoxylated fatty alcohol R is a $C_{12}$ to $C_{16}$ alkyl group and x averages from about 2 to about 6.

10. The process of claim 9 wherein the reaction pressure is from about 15 to 350 mm of Hg.

11. The process in claim 1 wherein the reaction pressure is from about 15 to 350 mm of Hg.

12. The process of claim 1 which converts more than about 85% of the ethoxylated fatty alcohol to the alkyl ethoxy carboxylate surfactant.

13. The process of claim 1 wherein, initially, the ethoxylated fatty alcohol is reacted with the hindered base and, subsequently, the resulting product is reacted with the anhydrous chloroacetic acid or the alkali metal salt or alkaline earth metal salt thereof.

14. The process of claim 1 wherein the reaction temperature is about 90° C. and the reaction pressure is from about 15 to 350 mm of Hg.

15. A process for preparing an alkyl ethoxy carboxylate surfactant of the formula $$RO(CH_2CH_2O)_xCH_2COO^-M^-$$

wherein R is a $C_8$ to $C_{18}$ alkyl group, x is a number averaging from 1 to 15, and M is an alkali metal or an alkaline earth metal cation; said process comprising, reacting:
   (a) an ethoxylated fatty alcohol of the formula $RO(CH_2CH_2O)_xH$, wherein R is a $C_8$ to $C_{18}$ alkyl group and x is a number averaging from about 1 to 15;
   (b) a hindered base of the formula $RO^-M^+$, wherein $RO^-$ is a secondary or tertiary alkoxide, R is a non-linear $C_4$ to $C_{12}$ alkyl group with at least one site of branching within 3 carbon atoms of the oxygen atom, and M is an alkali metal or alkaline earth metal cation; and
   (c) anhydrous chloroacetic acid, at a molar ratio of the hindered base to the anhydrous chloroacetic acid of 2:1, or an alkali metal salt or alkaline earth metal salt of anhydrous chloroacetic acid, at a molar ratio of the hindered base to the alkali metal salt or alkaline earth metal salt of chloroacetic acid of 1:1;
wherein the molar ratio of the ethoxylated fatty alcohol to the anhydrous chloroacetic acid or the alkali metal salt or alkaline earth metal salt thereof is from about 1:1 to about 1:1.15, the temperature is from 76.7° C. to 104.4° C., and the pressure is from 15 to 350 mm Hg.

16. The process of claim 15 wherein the ethoxylated fatty alcohol R is a $C_{12}$ to $C_{16}$ alkyl group and x averages from 2 to 6.

17. The process of claim 16 wherein the hindered base is a tertiary alkoxide salt.

18. The process of claim 17 wherein (c) is potassium chloroacetate, sodium chloroacetate, or a combination thereof.

* * * * *